US008306774B2

(12) United States Patent
Quinn et al.

(10) Patent No.: US 8,306,774 B2
(45) Date of Patent: Nov. 6, 2012

(54) THERMOMETER FOR DETERMINING THE TEMPERATURE OF AN ANIMAL'S EAR DRUM AND METHOD OF USING SAME

(76) Inventors: David E. Quinn, Auburn, NY (US); John A. Lane, Weedsport, NY (US); Scott A. Martin, Warners, NY (US); Craig M. Meyerson, Syracuse, NY (US); Matthew D. Mullin, Memphis, NY (US); Henry J. Smith, III, Auburn, NY (US); Ray D. Stone, Camillus, NY (US)

( * ) Notice: Subject to any disclaimer, the term of this patent is extended or adjusted under 35 U.S.C. 154(b) by 343 days.

(21) Appl. No.: 12/610,760

(22) Filed: Nov. 2, 2009

(65) Prior Publication Data
US 2011/0106484 A1 May 5, 2011

(51) Int. Cl.
G01K 11/30 (2006.01)
G01K 5/00 (2006.01)
G10K 7/00 (2006.01)

(52) U.S. Cl. .......................... 702/135; 374/121; 374/164
(58) Field of Classification Search .................. 702/135; 374/121, 164
See application file for complete search history.

(56) References Cited

U.S. PATENT DOCUMENTS

| 4,521,772 A | 6/1985 | Lyon |
| 4,521,773 A | 6/1985 | Lyon |
| 6,030,117 A | 2/2000 | Cheslock et al. |
| 6,272,375 B1 * | 8/2001 | Katzir et al. .................. 600/474 |
| 6,626,568 B2 | 9/2003 | Sato et al. |
| 7,314,310 B2 | 1/2008 | Medero |
| 7,434,992 B2 | 10/2008 | Tabata et al. |
| 2002/0143257 A1 * | 10/2002 | Newman et al. .............. 600/474 |
| 2002/0193703 A1 | 12/2002 | Sato et al. |
| 2004/0233968 A1 * | 11/2004 | Tabata et al. .................. 374/121 |
| 2005/0002437 A1 | 1/2005 | Fraden |
| 2005/0249263 A1 | 11/2005 | Yerlikaya et al. |
| 2007/0242726 A1 * | 10/2007 | Medero ......................... 374/164 |
| 2009/0182526 A1 | 7/2009 | Quinn et al. |

FOREIGN PATENT DOCUMENTS

| JP | 2005224617 A | 8/2005 |
| WO | WO 2009/041912 A1 | 4/2009 |

OTHER PUBLICATIONS

Tyco/Healthcare; Kendall GENIUS2 Infrared Tympanic Electronic Thermometer; 2006; pp. 1-13; Tyco Healthcare Group LP; USA.
International Search Report/Written Opinion for PCT Application No. PCT/US2010/053718; mailed May 26, 2011; 8 pages.
Notification of Transmittal of The International Search Report and The Written Opinion of the International Searching Authority, or The Declaration; 11 pages; Jul. 8, 2011.
Search History, 5 pages, Jul. 8, 2011.

* cited by examiner

*Primary Examiner* — Cindy H Khuu
*Assistant Examiner* — Manuel Rivera Vargas

(57) ABSTRACT

A thermometer for determining the temperature of an animal's ear drum. The thermometer includes a probe, an infrared-radiation detector adapted to receive infrared radiation emitted by the ear drum, and devices that help insure that the probe is disposed in a desired position in the ear canal so as to optimize the infrared radiation received from the ear drum, and to minimize the infrared radiation received from other ear parts. A method of using the thermometer is also disclosed.

20 Claims, 11 Drawing Sheets

US 8,306,774 B2

THERMOMETER FOR DETERMINING THE TEMPERATURE OF AN ANIMAL'S EAR DRUM AND METHOD OF USING SAME

FIELD OF THE INVENTION

The present invention relates to a thermometer for determining the temperature of an animal's ear drum and a method of using such thermometer. The thermometer senses infrared radiation emitted by the ear drum and the amount of infrared radiation detected is correlated with an associated temperature. The thermometer may include various devices for measuring the thermometer position with respect to the ear canal so that an accurate reading of the temperature of the ear drum may be obtained.

BACKGROUND OF THE INVENTION

The core body temperature is the operating temperature of an organism in deep structures of the body such as the liver, in contrast to temperatures of peripheral tissues such as the organism's skin. The core body temperature of a warm-blooded animal such as a human is usually a strong indicator of the state of the animal's health. For example, the condition of a high temperature is often caused by an infectious disease, and similarly, a high temperature may also indicate that the animal is suffering from a heat stroke. Such conditions, if not treated properly and quickly, may lead to more serious medical conditions and can result in a fatality.

While it is known that the core body temperature of a human tends to have the lowest value in the second half of the sleep cycle and that a human's body temperature typically changes by about 0.5 degrees Celsius (0.9 degrees Fahrenheit) between its highest and lowest points each day, it is important to monitor frequently any significant trends in the individual's core body temperature, such as to assess whether a particular medical treatment is working sufficiently quickly and favorably.

Typically, there have been four methods of trying to obtain the core body temperature of a warm-blooded animal such as a human. First, an oral thermometer may be placed in the mouth. Temperatures taken by this method, however, may be influenced by drinking, eating, or breathing. A second method is to take the temperature of the animal's underarm. Unfortunately, the temperature of the underarm may be vastly different from the core body temperature because the thermometer is placed next to the skin, which is a tool the body uses to control core body temperature. Moreover, skin temperatures are often influenced by factors such as medication, clothing, and external temperature. A third method has been the use of rectal thermometers. Such thermometers are not conveniently administered, often pose psychological discomfort, and present a contamination risk. The fourth method is the use of ear thermometers that measure the temperature of the tympanic membrane a/k/a the ear drum. Such ear thermometers typically involve detecting infrared radiation emitted from the ear drum.

Infrared thermometry is based upon the principle that all material emits electromagnetic radiation as so-called "blackbody" radiation. The emission spectrum, that is, the intensity of the radiation at each wavelength in a continuum of wavelengths, is in accord with Plank's law. For materials at about 60 degrees F. to 100 degrees F., their emission spectra tend to peak in the mid-infrared range, at wavelengths around 10 microns. The intensity of emission is proportional to temperature, and therefore, the temperature of a material can be determined by measuring its infrared emission. Such infrared radiation can be detected by any one of a number of different types of sensors such as thermopiles, pyroelectric sensors, and other types of infrared sensors.

An infrared ear thermometer can be used quickly and easily in a hospital or at home, is not embarrassing to use, and avoids contamination from re-use. Nevertheless, various factors can significantly affect the accuracy of temperature readings obtained by detecting infrared radiation emitted from the ear drum. For example, temperature readings can be affected by a relatively cold outer ear or ear canal, a hairy ear canal, or the presence of possible disease or infection. Moreover, due to variations in physical attributes of ear canal geometry or a defective positioning technique, the temperature readings may be skewed.

The present invention helps insure that the infrared radiation probe inserted into the ear canal is pushed deep enough into the ear canal so as to minimize the effects of the outer ear and ear canal temperature, to minimize the affect of physical contours of and hair within the ear canal, and to direct the probe toward the ear drum, without contacting the ear drum.

SUMMARY OF THE INVENTION

The present invention relates to a thermometer for determining the temperature of an animal's ear drum. The thermometer includes a probe, an infrared-radiation detector adapted to receive infrared radiation emitted by the ear drum, and devices that help determine the probe's position in the ear canal so as to optimize the infrared radiation received from the ear drum, and to minimize the infrared radiation received from other ear parts. A method of using the thermometer is also disclosed.

BRIEF DESCRIPTION OF THE DRAWINGS

The invention will be described with reference to the accompanying drawings, wherein.

DESCRIPTION OF A PREFERRED EMBODIMENT

Figure 1:
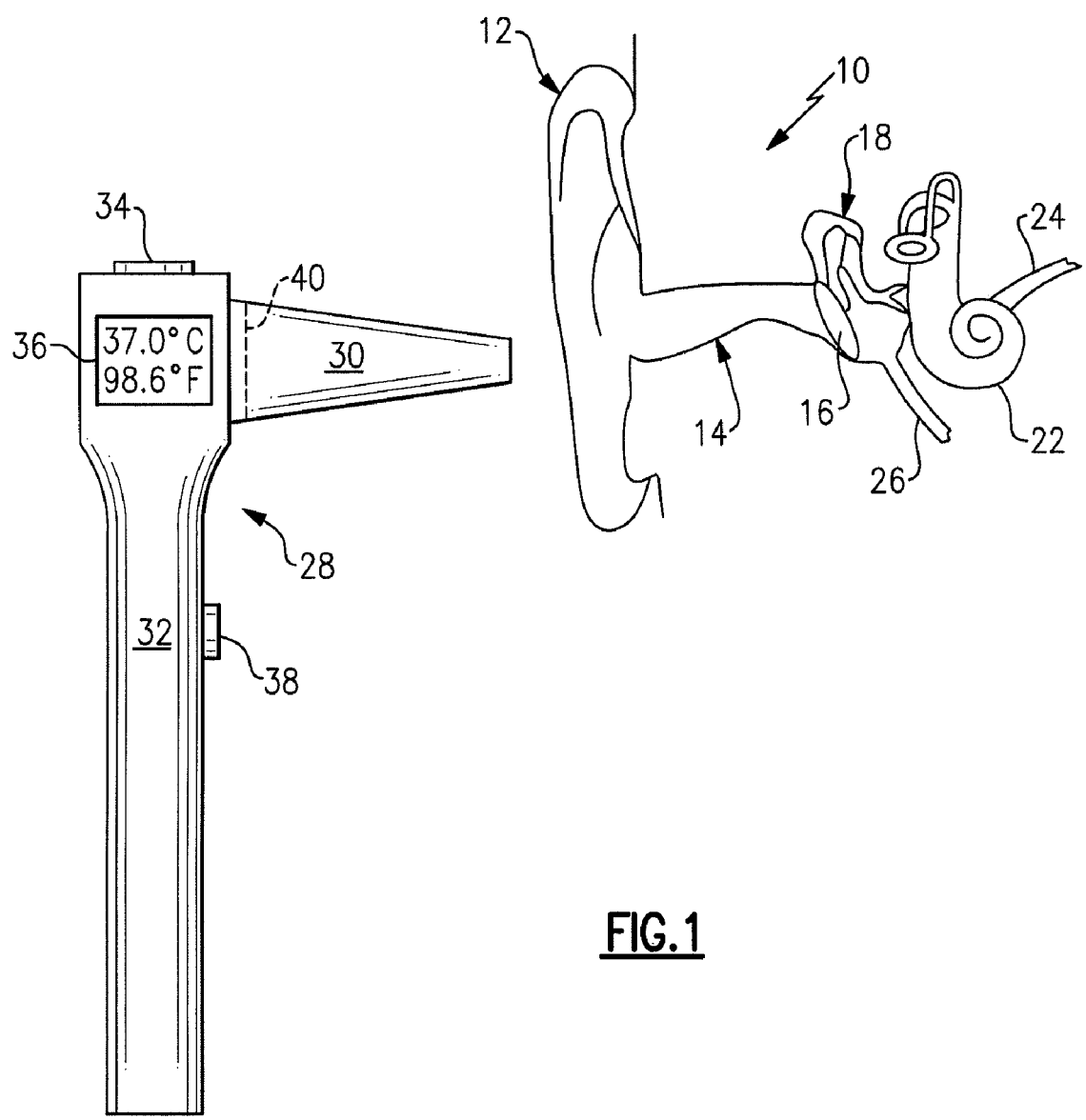
FIG. 1 is a schematic illustration of the principal components of a human's ear along with a plan view of a thermometer constructed in accordance with an embodiment of the present invention.

The present invention will be described with reference to the accompanying drawings wherein like reference numerals refer to the same item. It should be appreciated that the following description is intended to be exemplary only and that the scope of the invention envisions other variations and modifications of these particular exemplary embodiments.

There is shown in FIG. 1, in general illustration, the components of a human ear 10. An outer portion of the ear 10 known as the pinna 12 is formed of cartilage and is adapted to channel sound waves to the so-called ear canal 14, where the vibrations are directed onto the ear drum 16. The vibrations are further transmitted from the ear drum 16 through three tiny bones known as the ossicles 18, commonly known as the hammer, anvil, and stirrup, to the cochlea 22. The auditory nerve 24 connects the cochlea 22 to the brain. The region interior to the ear drum 16 opens to the Eustachian tube 26, which helps to maintain an even air pressure on each side of the ear drum 16.

Figure 2:
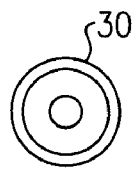
FIG. 2 is a longitudinal end view of a substantially frusto-conical probe that may be used in connection with the present invention.

There is shown in FIG. 1 a thermometer 28 that is fashioned generally in the shape of an otoscope, although other configurations are contemplated within the scope of the present invention. The thermometer 28 includes a frusto-conical speculum or probe 30 and a handle section 32 upon which are mounted a top display panel 34, a side display panel 36, and a manually activated push button 38. As will be appreciated from reviewing FIG. 1, the smaller end of the frusto-conical probe 30 is adapted to be inserted relatively deep into the ear canal 14, however, an intermediate section of the probe 30 is adapted to abut the outer-most portion of the ear canal 14 at a point where the smaller end of the probe 30 does not contact the ear drum 16. Probe configurations other than frusto-conical are also contemplated within the scope of the present invention. For example, the probe 30 may be more funnel-shaped with a smaller end that is substantially cylindrical. As shown in FIG. 2, which is an end view of the probe 30, the probe 30 is preferably hollow and possesses a relatively thin wall. As such, the opening in the smaller end of the probe 30 provides an opening through which the infrared radiation emitted by the ear drum 16 may pass through the probe 30 to an infrared detector 40 that may be disposed in the thermometer 28 adjacent to the larger end of the probe 30. As such, the probe 30 acts as an optical waveguide to help transmit infrared radiation emitted by the ear drum 16 onto the infrared-radiation detector 40. Preferably the interior wall of the probe 30 is coated with a material that possesses a high reflectance to infrared radiation. It should be appreciated that within the scope of the present invention, the infrared-radiation detector 40 may be placed at various positions, including most preferably at the smaller end of the probe 30. It is further preferred that the probe 30 be detachable from the handle portion of the thermometer 28 for maintenance and cleaning, or even more preferably, for disposal so as to minimize any contamination problems from re-use. In a preferred embodiment, the thermometer 28 includes a disposable, infrared-transparent sleeve (not shown) configured to conformingly cover the peripheral surface of the probe 30 adapted to be inserted relatively deep into the ear canal. The use of a plurality of such sleeves allows the probe 30 to be re-used by discarding a sleeve after use and replacing the sleeve with a new, unused sleeve.

Prior to use, the thermometer 28 is calibrated so that an object of a known temperature emits radiation onto the infrared-radiation detector 40. The intensity of the infrared radiation detected will be associated with the known temperature of that object. Such calibration can be performed with regard to known temperatures over the normal range of core body temperatures associated with a human or other animal. Thus, the amount of infrared radiation impinging upon the infrared-radiation detector 40 will be correlated with a particular temperature, which may be displayed in both Celsius and Fahrenheit on either the top visual display 34 or the side visual display 36, or both. It should also be appreciated that the thermometer 28 may be provided with a wired or wireless transmitter that provides the correlated temperature to a remote device that monitors, further processes, or records the temperature.

Figure 3:
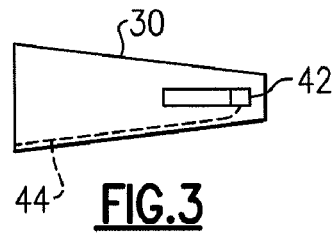
FIG. 3 is a side view illustration of the probe shown in FIG. 2 bearing a sliding movement sensor, such as a component of a conventional optical mouse.

There is shown in FIG. 3 a probe 30 on which is mounted an optical recognition sensor 42, that is a common component of an optical mouse. The sensor 42 is preferably placed on the exterior surface of the small end of the probe 30. The sensor 42 may possess a wide range of selected sizes, and may be placed at various regions around the small end of the probe 30, and may continuously extend around the small end of the probe 30.

Optical mice are commonly used for desktop personal computers over a pad or other surfaces to help move and guide a cursor arrow appearing on the computer screen. Early versions of mice utilized a rolling ball. Movement of the ball was translated with the arrow appearing on the computer screen. Later versions have utilized optical mice that often use light-emitting diodes and photo diodes to detect movement relative to the underlying surface, rather than a moving part such as a ball.

One of the early pioneers of optical mice was Richard F. Lyon of Xerox Corporation, and the construction and the operation of his optical mice are described in his U.S. Pat. Nos. 4,521,772 and 4,521,773. Such optical mice work by using an optoelectronic sensor to take successive pictures of the surface on which the mouse operates or views. The optical mice illuminate the surface over which they track, again, using a light-emitting diode or a photo diode, which are photographed and analyzed for optical variances or textures. Changes between one image frame and the next are processed by the image processing part of a computer chip and translated into movement along two axes using an optical flow estimation algorithm. By monitoring the change of position of a pattern, texture, or other feature being photographed, the computer chip can calculate the acceleration, velocity, and position of the mouse relative to the surface being tracked.

In one embodiment of the present invention, the optical sensor 42 tracks only a single point or feature and determines how far the feature has moved relative to the sensor 42, that is, how far the probe 30 is being inserted into the ear canal 14.

In the context of the present invention, the preferred surface being tracked is the peripheral skin surface of the ear canal 14. A thermometer 28 of the present invention, utilizing a sensor 42, is thus capable of continually monitoring the progress of the insertion of the probe 30 into the ear canal 14. As shown in FIG. 3, the sensor 42 may be connected via a wire 44 disposed along either the inner wall, or the outer wall, of the probe 30 to a microprocessor located within the handle 32 of the thermometer 28, which may be programmed to analyze input from the sensor 42 and the infrared detector 40 to determine when the probe 30 and the sensor 42 were at a point of deepest penetration into the ear canal 14, to determine what the intensity of the infrared radiation detected by the infrared sensor 40 was at that time, and to correlate that intensity to a temperature, which may be displayed on either or both of the displays 34, 36.

The optical sensor 42 may utilize a sampling rate of 1,500 frames per second, which is an ample sampling rate to determine the point of farthest penetration. An optical sensor that is believed to be suitable for the foregoing application is made by Agilent, with the model number ADNS-2610.

The manually activated push button 38 may trigger a switch that commences the tracking by the optical mouse 42, which may continue over a fixed duration, such as four seconds. Alternatively, the push button 38 might be re-depressed to stop the tracking. Also this could be a partially or completely automatic process.

Figure 4:
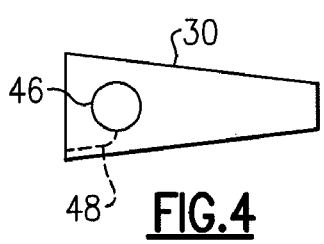
FIG. 4 is a side view illustration of the probe shown in FIG. 2 bearing an accelerometer in accordance with one embodiment of the present invention.

There is shown in FIG. 4 another embodiment of the present invention in which an accelerometer 46 is mounted on the exterior surface of the probe 30, near the large end thereof. As will be appreciated from reading the following description of this embodiment, the accelerometer 46 may be placed almost anywhere along the probe 30, and may even be placed on the handle portion 32 of the thermometer 28 and aligned with the probe 30. The accelerometer 46 may be connected via a wire 48 disposed along either the internal wall or the external wall of the probe 30 to an associated microprocessor disposed within the handle 32.

The accelerometer 46 measures acceleration and deceleration. Typically, the accelerometer 46 includes a mass disposed on a spring, and when the accelerometer (i.e., the mass) is moved, the spring will deflect. Most commonly, the capacitance between a set of fixed beams and a set of beams attached to the mass is measured. Alternatively, piezoresistors may be integrated into the springs to detect spring deformation.

By detecting how and when the spring is deflected, not only the acceleration, but also the speed, tilt and distance in one (axial) direction, two orthogonal directions, or three orthogonal directions, of the mass (i.e., the accelerometer) can be determined relative to a starting point.
Deflection of the spring may be measured in either an analog or a digital manner. Other types of accelerometers may also be advantageously employed in the context of the present invention.

Figure 5:
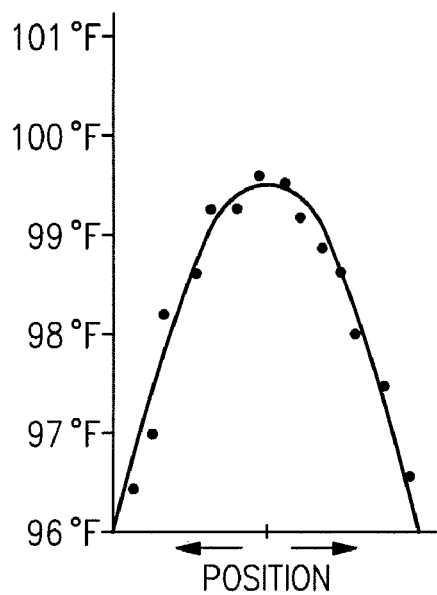
FIG. 5 is a graph of the signal obtained, which may be used to calculate the temperature of the ear drum using the probe shown in FIG. 4.

In the context of the present invention, the thermometer 28 is held such that the probe 30 is disposed only partially into the ear canal 14. The thermometer 28 is moved toward the ear canal 14 such that the probe 30 is inserted farther into the ear canal 14, and thereafter the thermometer 28 is withdrawn away from the ear canal 14. Again, a microprocessor in the handle 32 may receive input from the accelerometer 46 and the infrared-radiation detector 40 to determine when the probe 30 was at its deepest penetration into the ear canal 14 and to determine the intensity of the infrared radiation detected by the detector 40 at that time, which is correlated with a temperature and displayed in one or both of the displays 34, 36. Alternatively the microprocessor might chart the temperature over certain time intervals from the time of ear canal entrance until the thermometer 28 is withdrawn to the same position. An exemplary chart of temperature versus position in the ear canal 14 is depicted in FIG. 5. In order to select the definitive temperature of the ear drum, the microprocessor may be programmed to utilize an algorithm and plot a "best fit" curve. In FIG. 5, the curve is a parabola; one determines where there is a predetermined slope to the curve, and calculates the temperature of the ear drum 16.

An accelerometer that is believed to be useful in connection with the foregoing application is the ST LIS3L06AL three-axis linear accelerometer.

Figure 6:
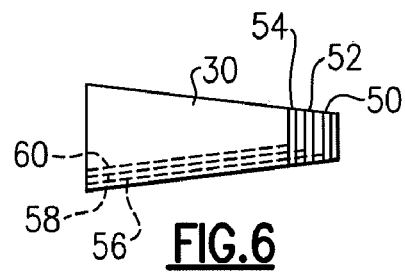
FIG. 6 is a side illustration of the probe shown in FIG. 2 bearing three spaced, electrically-conductive rings, in accordance with another embodiment of the present invention.

Yet another embodiment of the present invention is depicted in FIG. 6. One or more electrical conductors may be disposed about the periphery of the probe 30. In FIG. 6, there are three such electrical conductors 50, 52, 54 in the shape of rings that are disposed about the small end of the probe 30 in a spaced relationship. In a preferred embodiment, the electrical conductors may be fashioned of flat copper tape approximately one-eighth inch wide, and the electrical conductors may be coated with a polyimide film marketed under the name "Kapton", which provides an insulating and protective function. Each of the conductors 50, 52, 54 may be connected via an associated wire 56, 58, 60, respectively, and disposed within the hollow probe 30 to the interior of the handle 32 of the thermometer 28.

An A/C waveform generator 62 is applied to each of the respective conductors 50, 52, 54. As each of the conductors 50, 52, 54 is brought into closer proximity to the walls of the ear canal 14, the capacitance of the electrical conductors 50, 52, 54 changes. Generally, if no object is near the electrical conductors 50, 52, 54, then no current flows through the conductors 50, 52, 54, but current increasingly flows as the electrical conductors 50, 52, 54 get closer to an object, such as the inner wall of the ear canal 14. The current flow in each of the conductors 50, 52, 54 is measured by a current meter 64. It is believed that an Omron B6T workbench demo board may be utilized for this purpose. When the current flowing in each of the conductors 50, 52, 54 has reached a certain predetermined threshold associated with that conductor, then the temperature reading can be associated with that probe location. The temperature selected as defining the temperature of the ear drum 16 may be the first temperature reading that occurs after such threshold condition has been satisfied or may be the highest temperature reading within a time interval after such threshold condition has been satisfied and continues to be satisfied. Again, referring to FIG. 7, a microprocessor 66 may obtain input from both the current meter 64 and the infrared-radiation detector 40 to assess whether the threshold conditions have been achieved, to obtain readings of the infrared radiation impinging upon the infrared-radiation detector 40, and to display the selected temperature on one or both of the displays 34, 36.

Figure 7:
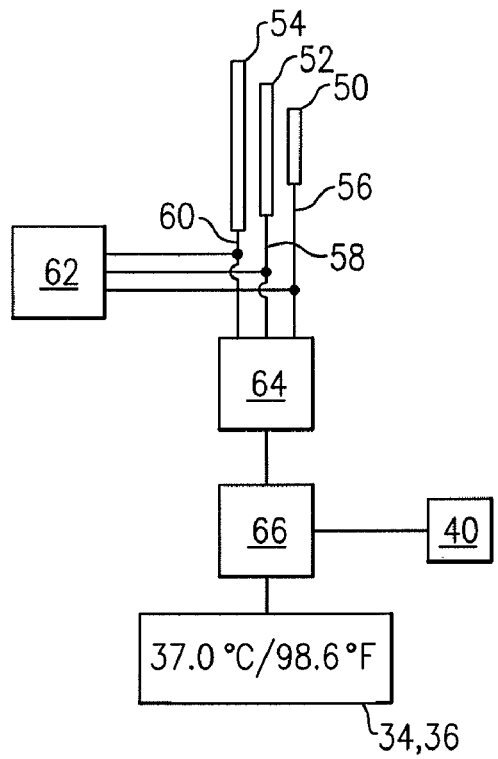
FIG. 7 is a schematic block diagram of the thermometer in accordance with the present invention utilizing the probe shown in FIG. 5.

A particular algorithm that may be used for determining the temperature of the ear drum will now be described utilizing the probe 30 as shown in FIG. 6 and the capacitance sensor shown in FIG. 7. In connection with explaining the algorithm, it is helpful to have an understanding of how the structure of an ear typically affects its temperature. The outer pinna 12 of the ear is exposed to the ambient air and includes very little blood flow. Consequently, the temperature of the pinna 12 tends to be significantly affected by the ambient temperature, although where the human or other animal has been exercising, the pinna 12 may have a relatively elevated temperature. At the entrance of the ear canal 14, the temperature tends to be affected by the pinna 12, by the bony skull 68, which is still relatively cool, since it contains relatively little blood and is close to the external skin, and also by the relatively high-temperature brain, which is blood rich and possesses a relatively high temperature. Deep in the ear canal, the ear canal wall is relatively thin, and the temperature is affected primarily by the brain and by the ear drum 16, which indicates the core body temperature.

Figure 8A:
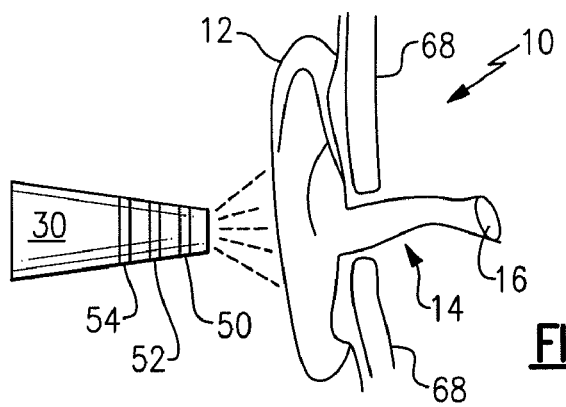
FIG. 8A is a schematic illustration of a probe with an infrared detector such as that shown in FIG. 6 approaching a human ear, with the dash lines indicating the field of "view" or sensing of the infrared detector.
Figure 8B:
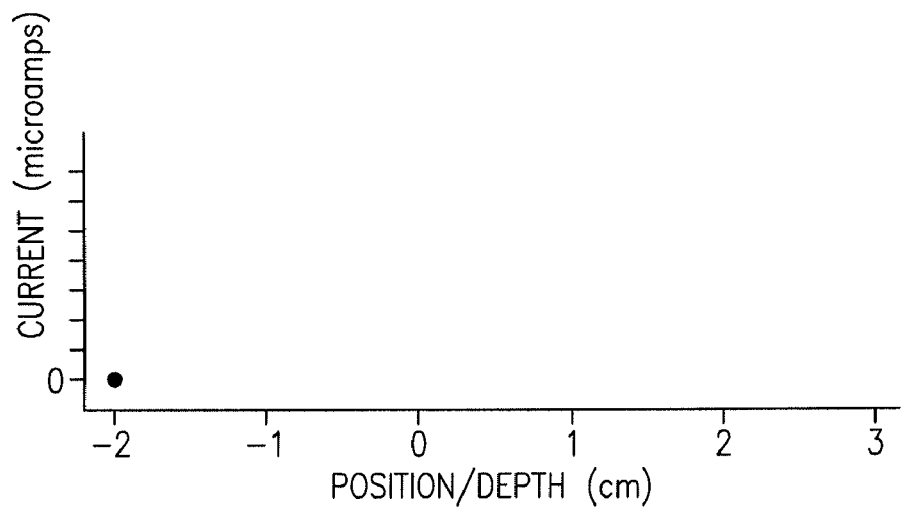
FIG. 8B is a graph indicating the current flowing through a capacitance sensor on the probe at a position relative to the ear canal.
Figure 8C:
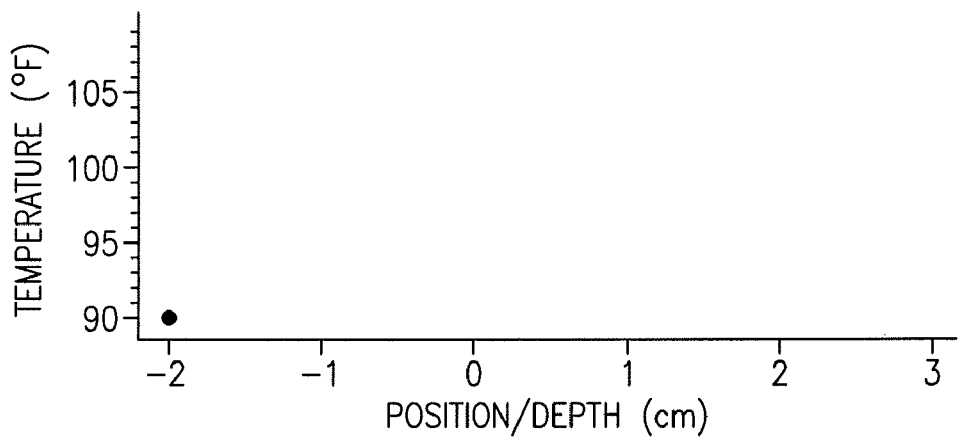
FIG. 8C is a graph indicating the corresponding temperature of the infrared radiation detected by the detector in the probe at a position relative to the ear canal.

As shown in FIG. 8A, when the probe 30 is positioned away from the pinna 12, the infrared detector in the probe 30 has a field of "view" or sensation of infrared radiation as depicted by the dash lines in FIG. 8A. The infrared detector senses and integrates infrared radiation emitted from objects in the entire field or view. Since the capacitance sensor on probe 30 is not in proximity to any animal tissue or other object, FIG. 8B shows the current flowing through the capacitance sensor will be zero. As shown in FIG. 8C, the amount of infrared radiation detected by the detector in the position shown in FIG. 8A will be greatly influenced by the ambient temperature, and in this example it is detected and correlated to be 90 degrees Fahrenheit.

Figure 9A:
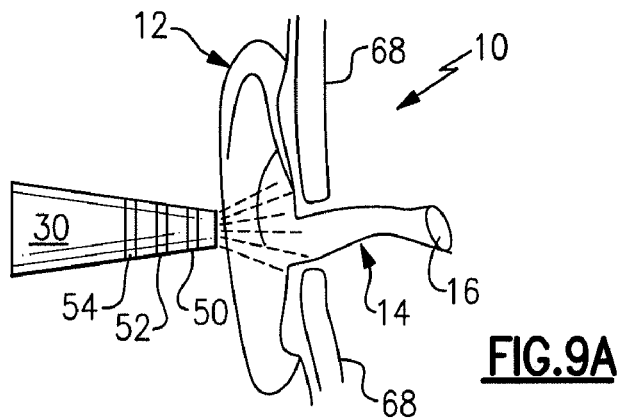
FIGS. 9A, 10A, 11A, and 12A illustrate the probe shown in FIG. 8A as it progresses toward and into the ear canal.
Figure 9B:
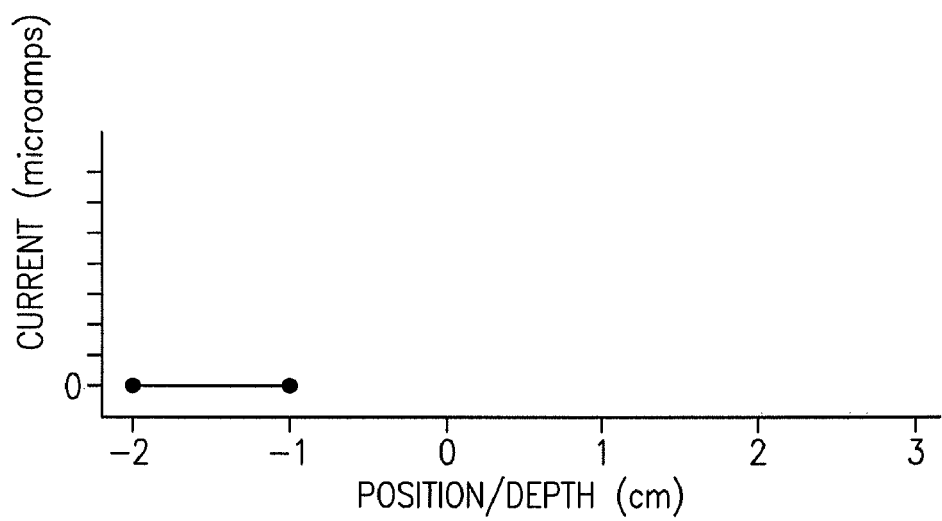
FIGS. 9B, 10B, 11B, and 12B are graphs corresponding to the graph in FIG. 8B and indicate the current flowing through the capacitance sensor as the probe is moved toward and enters into the ear canal.
Figure 9C:
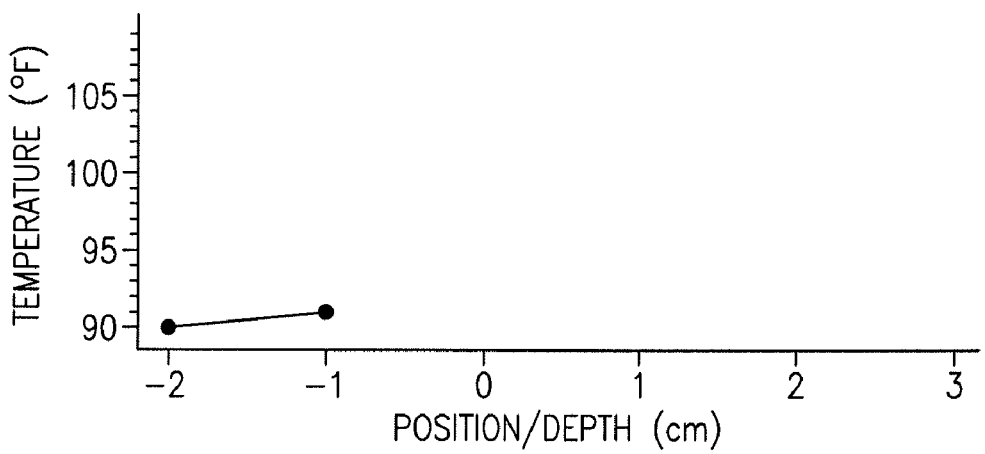
FIGS. 9C, 10C, 11C, and 12C are graphs corresponding to the graph in FIG. 8C and indicate the temperature corresponding to the infrared radiation detected by the probe as the probe is moved toward and enters into the ear canal.

As shown in FIG. 9A, the probe 30 is moved closer to the ear canal, but the current flowing through the capacitance sensor is still zero (FIG. 9B), and the temperature has risen only a single degree, to 91 degrees Fahrenheit (FIG. 9C).

Figure 10A:
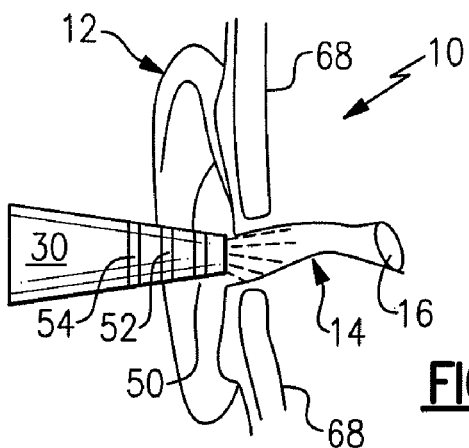
Figure 10B:
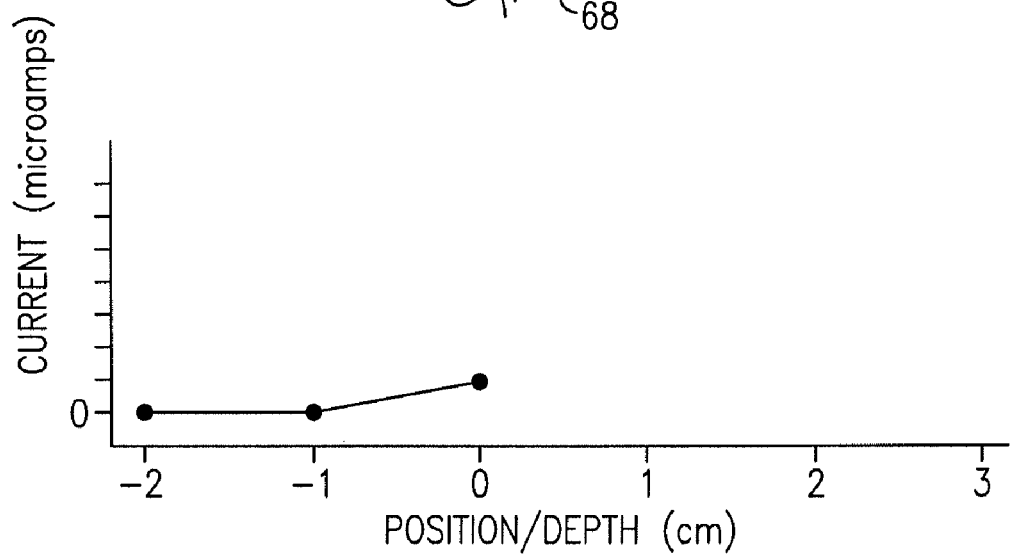
Figure 10C:
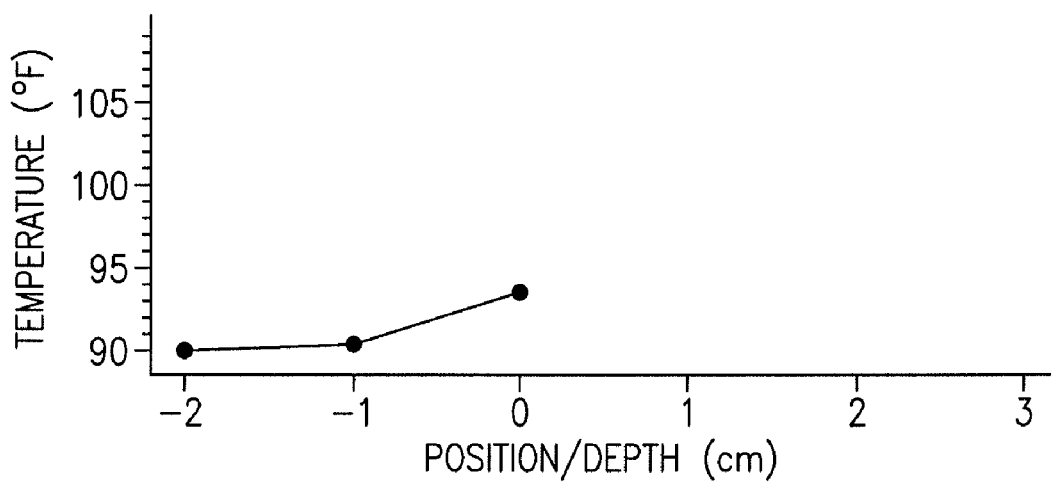

FIG. 10A depicts the small tip of the probe 30 exactly at the entrance of the ear canal 14. In this position, there will be a small current flow through the capacitance sensor, as indicated by FIG. 10B. Through empirical data testing of the probe 30 fitted with the capacitance sensor, the current flowing through the capacitance sensor where the probe tip is exactly at the entrance of the ear canal will be selected as a threshold current flow, and will define a so-called "zero" distance position relative to the ear canal 14. Similarly, other rates of current flow may be empirically tested and correlated with a distance of the tip of the probe 30 in the ear canal. As shown in FIG. 10C, the temperature detected by the probe 30 in the position shown in FIG. 10A has risen to 94 degrees Fahrenheit.

Figure 11A:
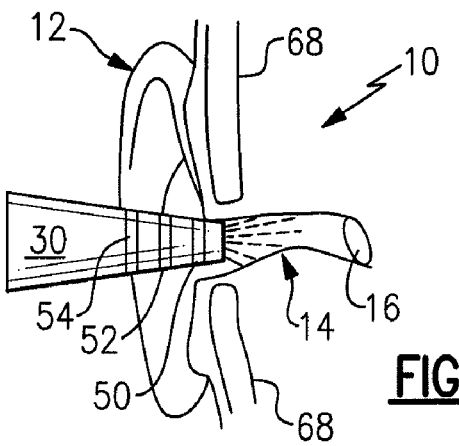
Figure 11B:
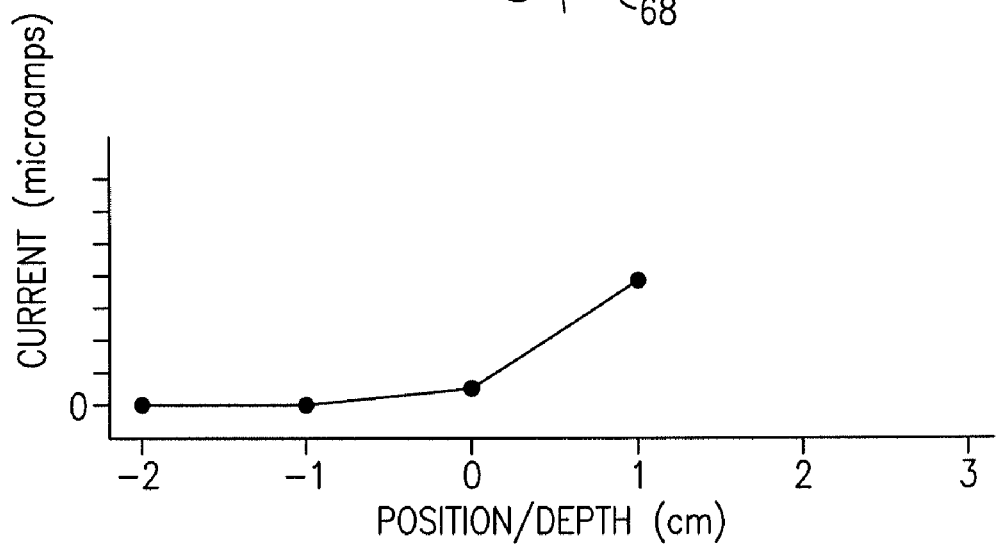
Figure 11C:
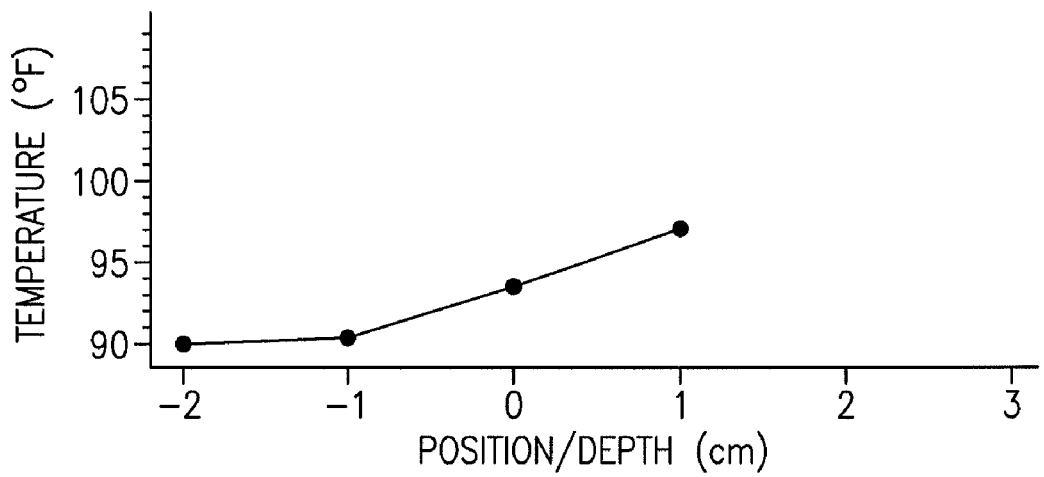

The tip of the probe 30 shown in FIG. 11A has been inserted a distance of one centimeter deep into the ear canal 14 from the entrance of the ear canal 14. As shown in FIG. 11B, the current flowing through the capacitance sensor has significantly increased because of the proximity of ear tissue to the capacitance sensor. As shown in FIG. 11C, the detected temperature has risen to 97 degrees Fahrenheit.

Figure 12A:
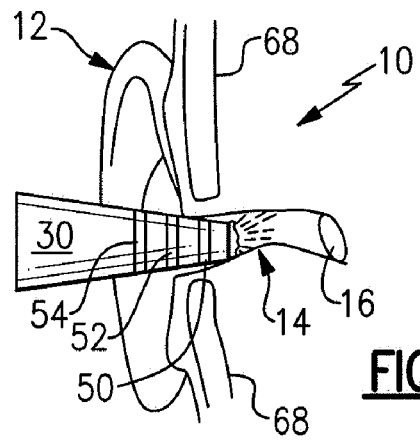
Figure 12B:
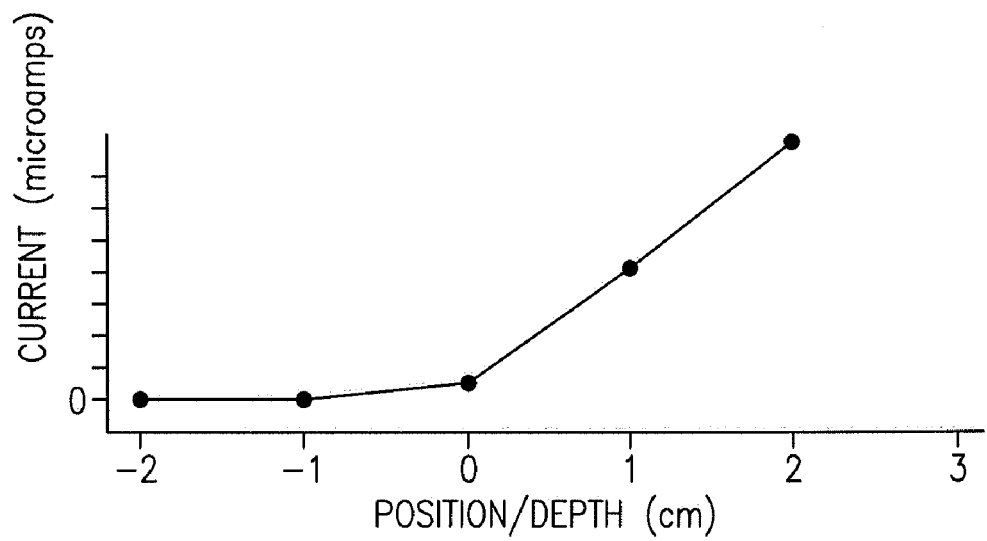
Figure 12C:
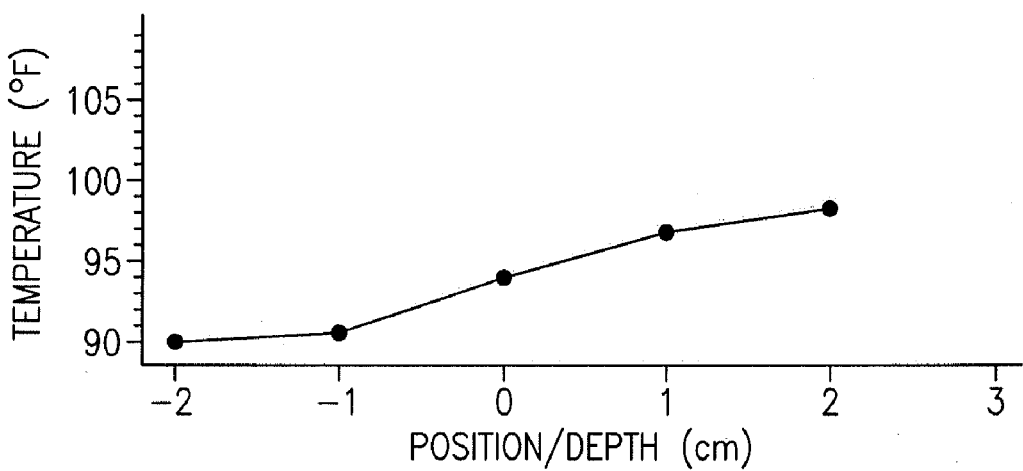

The position of the tip of the probe 30 shown in FIG. 12A is 2.0 centimeters into the ear canal 14 from the entrance to the ear canal 14. As shown in FIG. 12B, the current in the capacitance sensor has continued to rise. The temperature detected, as shown in FIG. 12C, has risen only slightly, to 98 degrees Fahrenheit.

Figure 14:
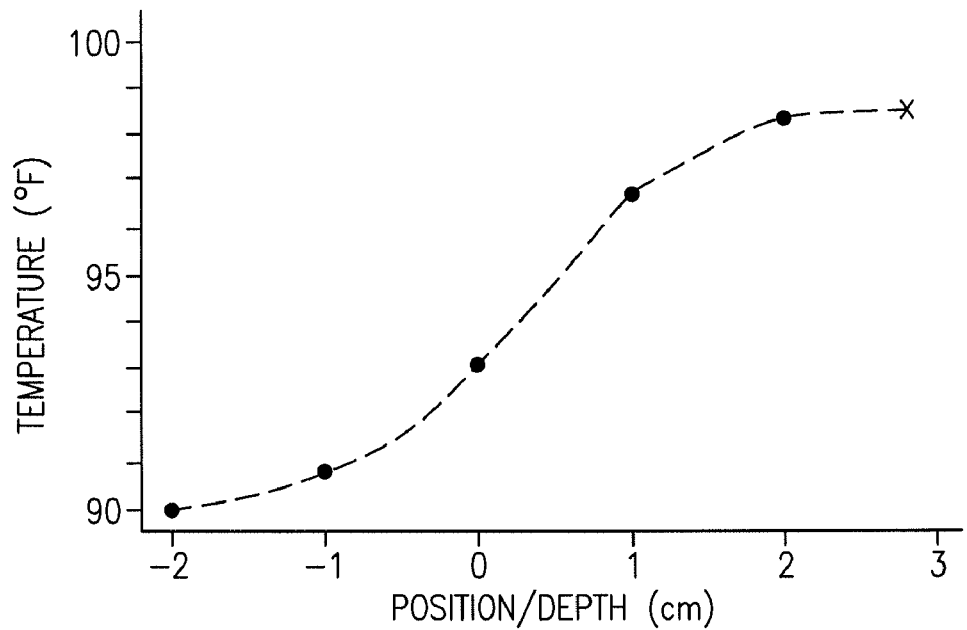
FIG. 14 is a graph indicating a typical curve of the temperature as sensed by the infrared detector as the detector approaches and enters into the ear canal.

FIG. 14 shows a typical plot of temperature detected by the infrared detector in the probe 30 where the "zero" distance indicates the entrance of the ear canal, where the ambient temperature around the pinna 12 is about 90 degrees Fahrenheit, and where the ear drum is 98.6 degrees Fahrenheit. Note that the slope of the plot is very shallow until about the position where the small tip of the probe 30 is at the entrance of the ear canal, then the slope is relatively steep from the "zero" position to about a one centimeter depth into the ear canal 14, and then the slope becomes very shallow at deeper penetrations into the ear canal beyond one centimeter.

Figure 13:
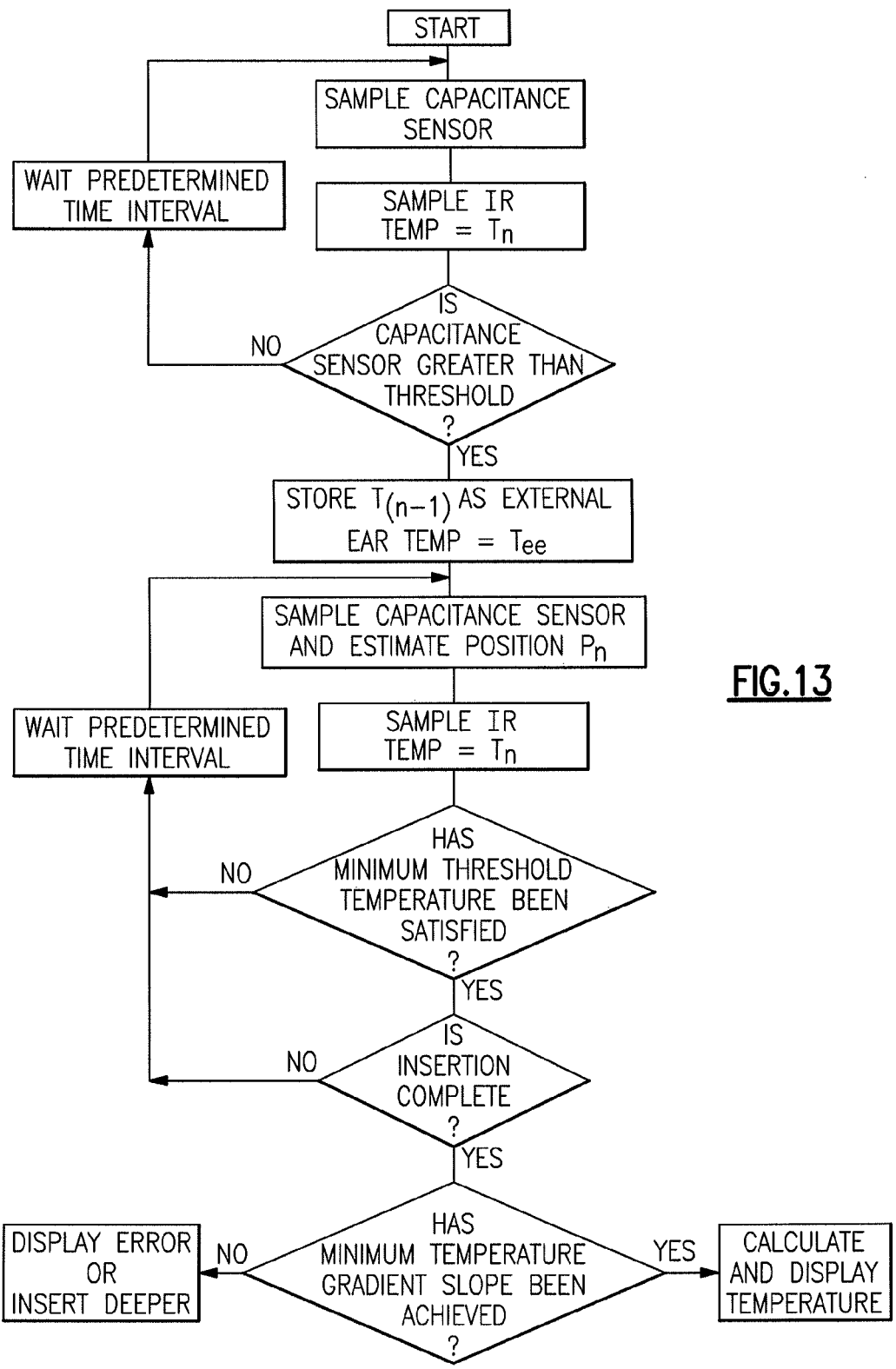
FIG. 13 is a flow chart indicating a sequence of how an estimate of the ear-drum temperature is determined in accordance with one embodiment of the present invention.

FIG. 13 shows a flow chart of sequences that can be used to determine an estimated temperature of the ear drum. The sequence may be started by depressing the push button 38, which initiates a sampling of the amperage flowing through the capacitance sensor. Such sampling may occur at essentially any rate, for example, ten samplings per second. The start also initiates a sampling of the amount of infrared radiation detected by the infrared-radiation detector, which may be correlated to a temperature. Again, the sampling may occur at essentially any rate, for example, ten samplings per second.

The sampling of the current flow through the capacitance sensor is analyzed to determine whether it has achieved the threshold current flow. If not, then a delay of a predetermined time interval, such as, for example, 100 milliseconds, occurs before the sampling of the current flow through the capacitance sensor and the sampling of the infrared radiation is re-initialized. If the current flow has achieved the threshold, then the temperature reading occurring when the threshold has been achieved is stored as the external ear temperature, $T_{EE}$.

Thereafter, the current flow of the capacitance sensor is continued to be sampled and an estimate of the position of the small tip of the probe 30 within the ear canal 14 is determined and the amount of infrared radiation, which correlates to a temperature, is also sampled corresponding to that particular position. The system may maintain a number of positions and temperature samplings, such as, for example, fifty samplings, with the first samplings being monitored, being the first samplings being discarded, as additional samplings are taken.

The system then determines whether a minimum threshold temperature, such as 93 degrees Fahrenheit, has been satisfied. If not, a delay of a predetermined time interval, such as, for example, 100 milliseconds, occurs and then the sampling is repeated, while maintaining the same external ear temperature reading. If the minimum threshold temperature has been achieved, then a determination is made as to whether the insertion of the probe has been completed. Such a determination may be made either by depressing the push button 38 or by selecting a predetermined distance or estimated position of the probe 30 within the ear canal as determined by the current flow through the capacitance sensor. If the insertion is not complete, then again, a delay of a predetermined time interval, such as, for example, 100 milliseconds, occurs and the sampling is repeated, again, while maintaining the same external ear temperature reading. If the insertion is complete, then the system determines whether a minimum temperature change gradient, that is, a minimum slope of temperature versus distance has been achieved. In other words, the system determines whether, after achieving a minimum threshold temperature, a relatively shallow temperature slope, such as that shown in the region beyond one centimeter in FIG. 14, has been achieved. If such a minimum temperature gradient has not been achieved, then the system displays 34, 36 display a message such as "error" or "invalid" or "insert deeper" in the displays 34, 36. If the minimum threshold gradient has been achieved, then the system calculates an estimated ear drum temperature and displays that temperature on the displays 34, 36 according to the following algorithm:

$$T_{ED} = T_{ID} + ((T_{ID} - T_{EE}) \times a) + (dy/dx \times (B - ID))$$

where
- $T_{ID}$ is the infrared sensed temperature at the deepest point of insertion into the ear canal
- $T_{EE}$ is the temperature immediately external to the ear canal entrance
- a is a correction factor based upon empirical testing and should typically be on the order of one one-hundredth (0.01)
- dy/dx is the slope or gradient of the temperature rise at the deepest point of insertion into the ear canal
- ID is the deepest point of insertion into the ear canal from a point where the probe first enters the ear canal
- B is the ideal insertion depth (typically 2.0 cm for adults and 1.0 cm for a child)

It should be recognized here that the distance from the entrance of the ear canal 14 to the ear drum 16 varies from animal to animal, and among humans. For example, the length of the ear canal 14 in a human adult is about 2.6 centimeters and for a human child it is much shorter. Consequently, the algorithm should be customized for a particular animal or size of human. The current invention contemplates that the thermometer 28 may be provided with a switch on the handle 32 for changing the factor "B". For example, one position of the switch may indicate "under 2 years old" or "under 20 pounds", which switch position will cause the factor "B" to equal 1.0 centimeters. A second position of the switch will be indicated with a legend "3-9 years old" or "20-90 pounds" and will correspond to a "B" value of 1.5 centimeters, and a third position of the switch will be indicated with a legend "over 10 years old" or "over 90 pounds", and will cause the "B" value to equal 2.0 centimeters.

It will be appreciated that the sequence shown in FIG. 13 and the above-recited formula or algorithm may be performed utilizing a microprocessor contained within the handle 32 of the thermometer 28.

Figure 15:
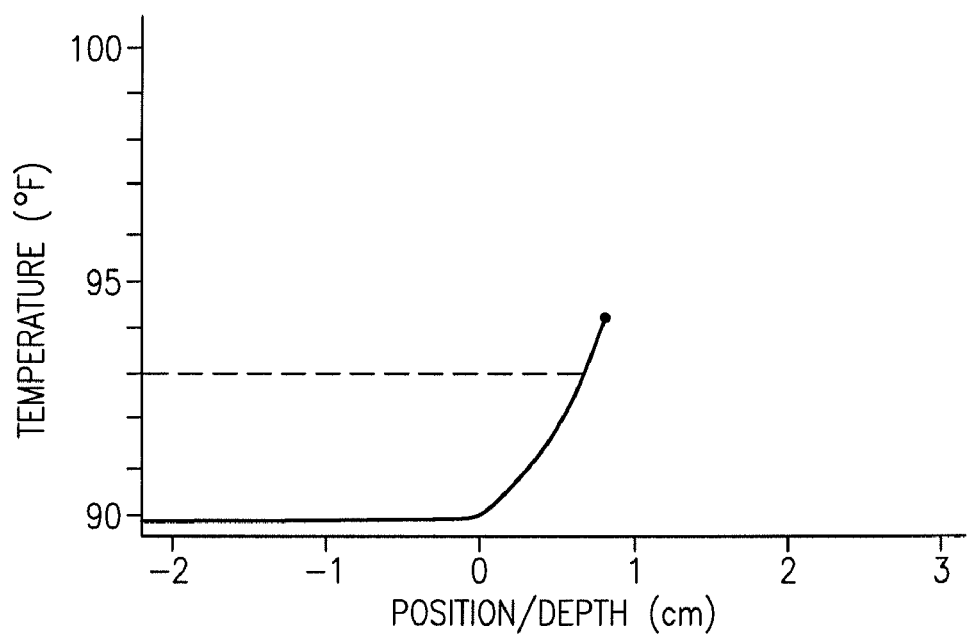
FIG. 15 is a graph of an attempted temperature reading taken when the probe is about 0.7 centimeters into the ear canal.

An example of how the sequence may operate will be demonstrated with reference to FIG. 15, which shows that prior to the probe 30 approaching the entrance of the ear canal 14, the infrared temperature reading was about 89.5 degrees Fahrenheit. At a distance of about 0.8 centimeters into the ear canal 14, the temperature has risen to about 94 degrees Fahrenheit. Even though a minimum threshold temperature, 93 degrees Fahrenheit, has been achieved, and even if the operator of the thermometer 28 believes that the insertion has been complete, such as by depressing the push button 38, the estimated temperature of the ear drum will not be calculated, but rather, a message such as "error" or "invalid" or "insert deeper" will be displayed on the displays 34, 36 because only a relatively steep temperature gradient has occurred after the minimum threshold temperature was achieved. Stated in other words, after the minimum threshold temperature was achieved, the slope of temperature versus distance has not sufficiently "flattened".

Figure 16:
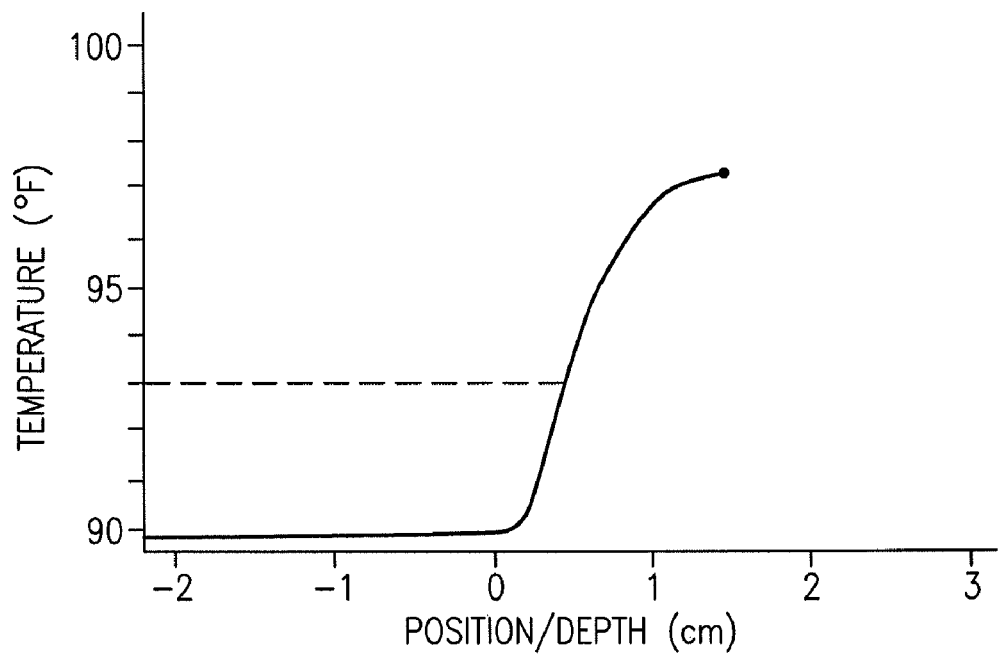
FIG. 16 is a graph of the temperature reading as the probe is about 1.3 centimeters into the ear canal.

FIG. 16 depicts an exemplary situation in which the insertion depth is 1.3 centimeters, at which point the infrared temperature reading is 97.5 degrees Fahrenheit, and the slope of the temperature gradient at that point is 1.4 degrees Fahrenheit per centimeter, and in which the external ear temperature at the "zero" point is 89.5 degrees Fahrenheit. When utilizing the following parameters set forth below with the above-referenced formula or algorithm, the estimated ear drum temperature is 98.66 degrees Fahrenheit.

$$T_{ID} = 97.5°\ F.$$

$$T_{EE} = 89.5°\ F.$$

$$a = 0.01$$

$$dy/dx = 1.4°\ F/cm$$

$$ID = 1.3\ cm$$

$$B = 2.0\ cm$$

$$T_{ED} = 97.5°\ F. + ((97.5°\ F. - 89.5°\ F.) \times 0.01) +$$
$$(1.4°\ F/cm \times (2.0\ cm - 1.3\ cm))$$
$$= 97.5°\ F. + (0.08°\ F.) + (0.98°\ F.)$$
$$= 98.66°\ F.$$

Figure 17:
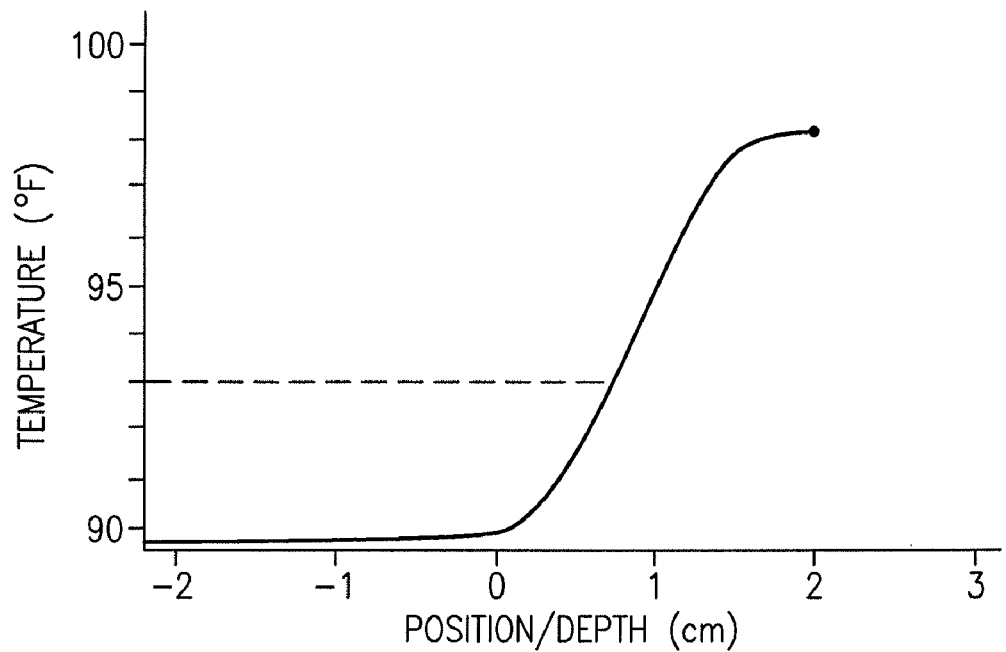
FIG. 17 is a graph of the temperature reading as the probe is about 2 centimeters into the ear canal.

Yet another example is depicted in FIG. 17, in which the insertion distance is 2.0 centimeters, the temperature gradient is 0.2 degrees Fahrenheit per centimeter, the temperature at the insertion depth is 98.5 degrees Fahrenheit, and the external ear temperature at point "zero" is 89.5 degrees Fahrenheit. When utilizing an "a" value of 0.01 and a "B" value of 2.0 centimeters and implementing the foregoing values in the aforementioned formula or algorithm, the estimated ear temperature is calculated as follows:

$$T_{ED} = 98.5°\ F. + ((98.5°\ F. - 89.5°\ F.) \times 0.01) +$$
$$(0.2°\ F/cm \times (2.0\ cm - 2.0\ cm))$$
$$= 98.5°\ F. + (0.08°\ F.) + (0°\ F.)$$
$$= 98.58°\ F.$$

Figure 18:
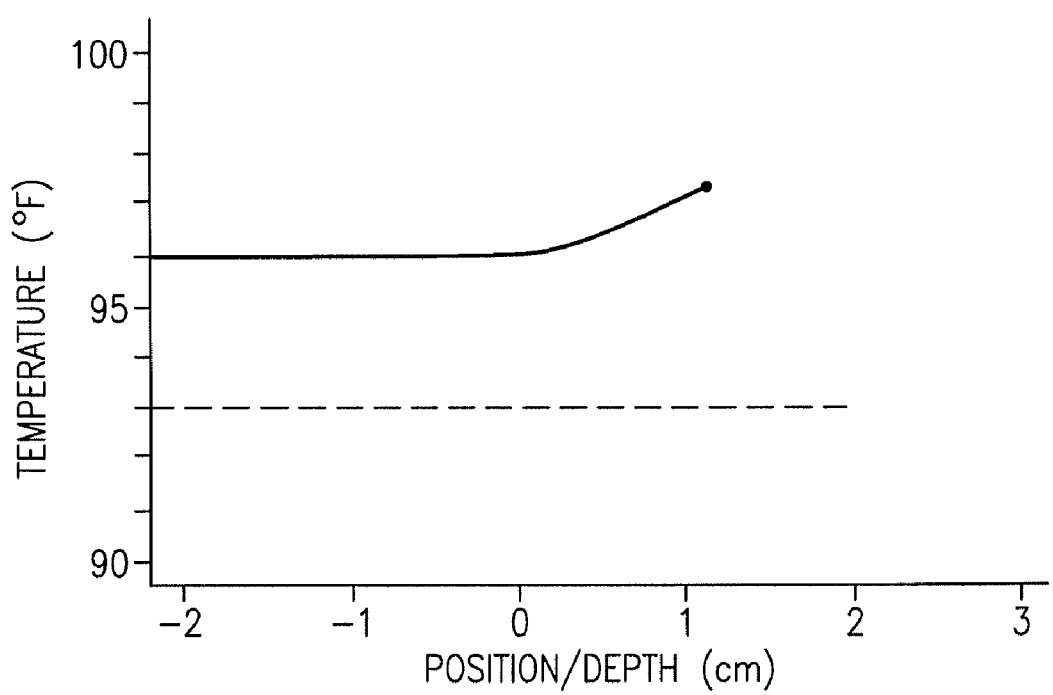
FIG. 18 is a graph of the temperature reading as the probe is inserted 1.0 centimeters into the ear canal, where the ambient temperature is relatively high.

A further example is shown in FIG. 18, in which the external ear temperature is relatively high, and equals 96.0 degrees Fahrenheit. The insertion depth is 1.0 centimeters, the temperature at that point is 97.5 degrees Fahrenheit, and the temperature gradient slope at that point is 1.1 degrees Fahrenheit per centimeter. Again, using an "a" value of 0.01 and a "B" value of 2.0 centimeters, the estimated ear drum temperature is calculated as follows:

$$T_{ED} = 97.5°\ F. + ((97.5°\ F. - 96.0°\ F.) \times 0.01) +$$
$$(1.1°\ F/cm \times (2.0\ cm - 1.0\ cm))$$
$$= 97.5°\ F. + (approx.\ 0°\ F.) + (1.1°\ F.)$$
$$= 98.6°\ F.$$

From the foregoing, it will be appreciated that a microprocessor may be operationally connected to the infrared detector and to the capacitance sensor circuitry and to the push button 38 to receive data that may be utilized in the sequence shown in FIG. 13 and that may be applied in accordance with the foregoing formula or algorithm to determine an estimation of the ear drum temperature.

The invention also contemplates that the same sort of process could be used during the withdrawal of the probe 30 from the ear canal in order to verify the accuracy of the data obtained during the insertion of the probe 30 into the ear canal. If the data obtained during withdrawal is different by more than a predetermined amount or ratio from the data obtained during insertion, then the ear drum temperature estimate may be declared suspect or invalid, and the operator may be urged or required to repeat the entire process.

As an optional feature, the probe 30 itself may be preheated to a select temperature, such as 90 degrees Fahrenheit, so that the temperature of the probe 30 itself will not have any significant effect on modifying the temperature of nearby tissue; otherwise, a relatively cold probe 30 might have a possible effect on the amount of infrared radiation emitted by such tissue. Such pre-heating may be achieved by placing any resistor-like material on the probe 30 and selectively applying an electric current from a battery located within the handle 32 of the thermometer 28 such as by selectively activating a switch located on the handle 32. The thermometer 28 could also be provided with a light indicator that emits light when the probe 30 is sufficiently pre-heated and ready for use. Such a light might be activated either after a pre-selected time or after another thermometer located in the probe 30 determines that the pre-selected temperature has been achieved.

While exemplary embodiments have been presented in the foregoing description of the invention, it should be appreciated that a vast number of variations within the scope of the invention may exist including other methods of determining probe insertion positioning. The foregoing examples are not intended to limit the nature or the scope of the invention in any way. Rather, the foregoing detailed description provides those skilled in the art with a foundation for implementing other exemplary embodiments of the invention.

We claim:

1. A thermometer for determining an estimated temperature of a vertebrate animal's ear drum, said thermometer comprising:
    a probe adapted to be inserted into an ear canal;
    a detector adapted to sense infrared radiation emitted by the ear canal, said detector being operatively coupled to said probe;
    a proximity sensor for determining the position of said probe with respect to the ear canal; and
    a microprocessor programmed to determine the temperature based upon a gradient of the magnitude of infrared radiation sensed by detector over different positions of the probe with respect to the ear canal by calculating substantially a best fit curve of a plurality of temperatures sensed by said detector versus position samples determined by said proximity sensor, calculating where the curve has a selected slope, and calculating the estimated temperature associated with a point where the selected slope occurs.

2. A thermometer according to claim 1 wherein said microprocessor is programmed to analyze proximity sensor input and detector input external to the ear canal in determining the estimated temperature.

3. A thermometer according to claim 2 wherein said proximity sensor includes an electrical conductor mounted on said probe, an A/C waveform generator operatively connected to said electrical conductor, and an electric current flow monitor operatively connected to said electrical conductor.

4. A thermometer according to claim 2 wherein said microprocessor uses input from the proximity sensor to define a position substantially near an entrance of the ear canal.

5. A thermometer according to claim 4 wherein said position is determined by the proximity sensor achieving a threshold current flow.

6. A thermometer according to claim 1 wherein said probe possesses a substantially frusto-conical configuration.

7. A thermometer according to claim 1 wherein said plurality of temperatures exceed three in number.

8. A method of determining a temperature of a vertebrate animal's ear canal and ear drum, said method comprising:
    providing an infrared-radiation detector;
    obtaining the temperature in an exterior vicinity of an entrance to an ear canal leading to the ear drum by using said detector;
    charting the temperature at a plurality of distances within the ear canal by using said detector;
    determining whether a minimum pre-selected temperature has been charted;
    determining whether a minimum pre-selected threshold temperature gradient has been charted;
    only if said minimum pre-selected temperature has been charted and only if said minimum temperature gradient has been charted, then using the obtained temperature, the temperature charted at substantially the greatest distance within the ear canal, and the temperature gradient at such greatest distance to determine the temperature of the ear drum.

9. A method of determining a temperature of a vertebrate animal's ear canal and ear drum according to claim 8, said method additionally comprising:
    if said minimum pre-selected temperature has not been charted, or if said minimum pre-selected temperature gradient has not been charted, then prohibiting the determination of the temperature of the ear drum.

10. A method of determining a temperature of a vertebrate animal's ear canal and ear drum according to claim 8 wherein the determined estimated temperature of the ear drum corresponds to an ear drum temperature that would be sensed by the detector at an insertion depth.

11. A thermometer for determining an estimated temperature of a vertebrate animal's ear drum, said thermometer comprising:
    a probe adapted to be inserted into an ear canal;
    a detector adapted to sense infrared radiation emitted by the ear drum, said detector being operatively coupled to the probe;
    a proximity sensor for determining the position of said probe with respect to the ear canal; and
    a microprocessor configured to determine the estimated temperature based upon a gradient of the magnitude of infrared radiation sensed by the detector over different positions of the probe with respect to the ear canal.

12. A thermometer according to claim 11 wherein the estimated temperature corresponds to an ear drum temperature that would be sensed by the detector at an ideal insertion depth.

13. A thermometer according to claim 11 wherein the microprocessor is also configured to determine a best fit curve of a plurality of temperatures sensed by the detector versus position samples determined by the proximity sensor.

14. A method of determining a temperature of a vertebrate animal's ear drum, said method comprising:
    providing a probe;
    providing an infrared-radiation detector operatively coupled to said probe;
    providing an electrical conductor connected to said probe for determining the position of said probe;
    inserting said probe into the animal's ear canal;
    determining the amount of infrared radiation detected by said infrared-radiation detector substantially when a deepest point of insertion occurs; and
    determining the temperature based upon a gradient of the magnitude of infrared radiation sensed by the detector over different positions of the probe with respect to the ear canal.

15. The method of claim 14, further comprising:
    delivering an A/C waveform into said electrical conductor as said probe is so inserted;
    measuring the current of electricity flowing through said electrical conductor as said probe is so inserted;

setting a threshold amount of electricity flow through said electrical conductor; and detecting substantially when a threshold amount of electricity flows through said electrical conductor to determine substantially when the deepest point of travel occurs.

16. A thermometer for determining a temperature of a vertebrate animal's ear drum, said thermometer comprising:
a probe adapted to be inserted into an ear canal;
a detector connected to said probe and adapted to sense infrared radiation emitted by the ear canal and the ear drum;
a proximity sensor for determining the position of said probe with respect to the ear canal; and
means operatively connected to said detector for determining a change in an amount of infrared radiation sensed by said detector as said detector is inserted into the ear canal and for declaring invalid, based upon the change, the temperature correlating to a gradient of the magnitude of infrared radiation sensed by the detector over different positions of the probe with respect to the ear canal.

17. A thermometer according to claim 16 wherein said determining means also is configured to analyze sensor input external to the ear canal in making the determination.

18. A method of determining a temperature of a vertebrate animal's ear drum, said method comprising:
providing a probe;
providing an infrared-radiation detector operatively coupled to said probe;
providing an accelerometer connected to said probe for determining the position of said probe;
inserting said probe into the animal's ear canal;
determining the amount of infrared radiation detected by said infrared-radiation detector substantially when a deepest point of insertion occurs; and
determining the temperature based upon a gradient of the magnitude of infrared radiation sensed by the detector over different positions of the probe with respect to the ear canal.

19. The method of claim 18, further comprising:
detecting with said accelerometer the motion of said probe being inserted into the ear canal; and
determining in response to the motion detection substantially when said probe has attained the deepest point of insertion.

20. A thermometer for determining an estimated temperature of a vertebrate animal's ear drum, said thermometer comprising:
a probe adapted to be inserted into an ear canal;
a detector adapted to sense infrared radiation emitted by the ear canal, said detector being operatively coupled to said probe;
a proximity sensor for determining the position of said probe with respect to the ear canal; and
a microprocessor programmed to determine the temperature based upon a gradient of the magnitude of infrared radiation sensed by the detector over different positions of the probe with respect to the ear canal by calculating substantially a best fit curve of a plurality of temperatures sensed by said detector versus position samples determined by said proximity sensor, calculating where the curve has a selected slope, and calculating the estimated temperature associated with a point where the selected slope occurs.

* * * * *

UNITED STATES PATENT AND TRADEMARK OFFICE
CERTIFICATE OF CORRECTION

PATENT NO. : 8,306,774 B2
APPLICATION NO. : 12/610760
DATED : November 6, 2012
INVENTOR(S) : David E. Quinn et al.

Page 1 of 1

It is certified that error appears in the above-identified patent and that said Letters Patent is hereby corrected as shown below:

In the Claims:

Column 11, line 35, should read as follows:

radiation sensed by --the-- detector over different positions of

Column 14, lines 14-32 should read as follows:

--20. A thermometer for determining a temperature of a vertebrate animal's ear canal and ear drum, said thermometer comprising:
 a probe adapted to be inserted into the ear canal;
 a detector adapted to sense infrared radiation emitted by the ear canal and the ear drum, said detector being operatively coupled to said probe;
 a sliding movement sensor for determining the position of said probe with respect to an ear canal, wherein said sliding movement sensor includes an optical recognition device adapted to detect changes in the surrounding portions of the ear canal as said probe is inserted into the ear canal; and
 a microprocessor configured to determine the temperature based upon a gradient of the magnitude of infrared radiation sensed by the detector over different positions of the probe with respect to the ear canal.--

Signed and Sealed this
Sixth Day of August, 2013

Teresa Stanek Rea
*Acting Director of the United States Patent and Trademark Office*